United States Patent [19]

Kelleher et al.

[11] Patent Number: 4,996,047
[45] Date of Patent: Feb. 26, 1991

[54] SUSTAINED RELEASE DRUG-RESIN COMPLEXES

[75] Inventors: William J. Kelleher, Storrs; Anthony E. Carpanzano, Sherman, both of Conn.

[73] Assignee: Richardson-Vicks, Inc., Shelton, Conn.

[21] Appl. No.: 265,910

[22] Filed: Nov. 2, 1988

[51] Int. Cl.$^5$ .................. A61K 31/74; A61K 9/14; A61K 9/52
[52] U.S. Cl. .................................. 424/79; 424/78; 424/486; 424/484; 424/483; 424/490; 514/964; 514/781
[58] Field of Search ............... 424/78, 79, 486, 484, 424/483, 490; 514/964, 781

[56] References Cited

U.S. PATENT DOCUMENTS

| | | |
|---|---|---|
| 2,990,332 | 6/1961 | Keating . |
| 3,138,525 | 6/1964 | Koff ........................ 167/55 |
| 3,155,590 | 11/1964 | Miller et al. .................... 167/83 |
| 3,499,960 | 3/1970 | Macek et al. ..................... 424/33 |
| 3,594,470 | 7/1971 | Borodkin ........................ 424/79 |
| 4,221,728 | 9/1980 | Raghunathan .................. 424/79 |
| 4,221,778 | 9/1980 | Raghunathan .................. 424/ |
| 4,389,331 | 6/1983 | Samejima et al. ............ 427/213.3 |
| 4,486,471 | 12/1984 | Samejima et al. ............ 427/213.3 |
| 4,788,055 | 11/1988 | Fischer et al. ................... 424/79 |
| 4,847,077 | 7/1989 | Raghunathan .................. 424/79 |

FOREIGN PATENT DOCUMENTS

| | | |
|---|---|---|
| 0249949 | 12/1987 | European Pat. Off. . |
| 0254811 | 3/1988 | European Pat. Off. . |
| 0254822 | 3/1988 | European Pat. Off. . |
| 2246037 | 9/1972 | Fed. Rep. of Germany . |
| 1218102 | of 0000 | United Kingdom . |

OTHER PUBLICATIONS

Journal of Pharmaceutical Science, vol. 60, pp. 1523–1527.

Primary Examiner—Johnnie R. Brown
Assistant Examiner—Carmen Pili-Curtis
Attorney, Agent, or Firm—David K. Dabbiere; Douglas C. Mohl; Jack D. Schaeffer

[57] ABSTRACT

Disclosed are oral pharmaceutical preparations which comprise a pharmacologically active drug bound to small particles of an ion-exchange resin to provide a drug-resin complex having a drug content above a specified value. The drug-resin complex is subsequently coated with a water-permeable diffusion barrier coating that is insoluble in gastrointestinal fluids thereby providing a controllable sustained release of drug under conditions encountered in the gastrointestinal tract.

16 Claims, No Drawings

SUSTAINED RELEASE DRUG-RESIN COMPLEXES

TECHNICAL FIELD

The present invention relates to oral pharmaceutical preparations which comprise a pharmacologically active drug bound to small particles of an ion-exchange resin to provide a drug-resin complex having a drug content above a specified value. The drug-resin complex is subsequently coated with a water-permeable diffusion barrier coating that is insoluble in gastrointestinal fluids thereby providing a controllable sustained release of drug under conditions encountered in the gastrointestinal tract.

BACKGROUND OF THE INVENTION

Sustained or prolonged-release dosage forms provide a controlled and constant supply of drug to an organism. The control of cough, sleep, enuresis, and migraine headaches are all benefits obtained from such a controlled release of a specific drug. Additionally, controlled release of antimicrobials can be obtained through such a dosage form. Such controlled release drugs eliminate the need to interrupt sleep to take medication, and can also prevent missed doses. They also provide the convenience of daytime dosing where the dosage form can be taken first thing in the morning and provide therapeutic levels of the drug throughout the day.

A controlled drug-release system delivers drugs in a manner that will maintain therapeutically effective plasma levels over a period of time that is significantly longer than that which is given by a typical drug dosage form.

Uncoated ion-exchange resin-drug complexes which delay release of a drug in the gastrointestinal tract are described in U.S. Pat. No. 2,990,332. However, such uncoated complexes provide only a relatively short delay of drug release in comparison with the preparations of this invention and provide poor control of drug release because the control is limited to variation in particle size and cross-linkage of the sulfonic acid-type resin used to prepare the adsorption compounds.

Various coated resin-drug complexes have been reported (e.g., in U.S. Pat. Nos. 3,138,525; 3,499,960 and 3,594,470; Belgian Pat. No. 729,827; German Pat. No. 2,246,037; and Borodkins et al, *Journal of Pharmaceutical Science*. Vol. 60, pages 1523-1527, 1971), but none are believed to employ the preparations of the subject invention or to provide the prolonged continuous release obtainable with the present preparations.

The present invention provides controlled-release pharmaceutical compositions obtained by complexing the drug with a pharmaceutically acceptable ion-exchange resin and coating such complexes with a substance that will act as a barrier to control the diffusion of the drug from its core complex into the gastrointestinal fluids.

It is known that the pharmaceutically acceptable resins and their drug complexes can undergo significant swelling (up to about a 60% increase in volume) when the dry, non-hydrated form is placed in contact with gastrointestinal fluids.

When the coated drug-resin complex is suspended in an aqueous dosage form or when it contacts gastrointestinal fluids, it expands to its swollen state, and in doing so, ruptures the diffusion barrier coating. The result is loss of control of the diffusion of released drug.

Controlled-release drugs for use in the gastrointestinal tract are described in U.S. Pat. No. 4,221,778 to Raghunathan, issued Sept. 9, 1980. The method described therein for preparing products having controlled release properties involved a three-step process: (i) preparation of a drug-resin complex; (ii) treating this complex with a suitable impregnating agent; and (iii) coating the particles of treated complex with a water-permeable diffusion barrier. The impregnation is necessary to provide the desired controlled-release of drug.

The present invention does not require any such impregnation and provides a coated drug-resin complex which, when placed in contact with an aqueous vehicle or with gastrointestinal fluids, does not undergo swelling sufficient to rupture the diffusion barrier coating. Without being limited by theory, Applicants have demonstrated that there is a critical drug load that must be achieved in order to assure maintenance of the integrity of the coating and therefore controlled release of the drug active.

It is therefore an object of the present invention to provide a drug-resin complex coated with a water-permeable diffusion barrier coating that is insoluble in gastrointestinal fluids thereby providing a controllable sustained release of drug under conditions encountered in the gastrointestinal tract.

It is a further object of the present invention to provide such a coated drug-resin complex which does not undergo swelling sufficient to rupture its diffusion barrier coating.

SUMMARY OF THE INVENTION

An oral pharmaceutical composition in unit dosage form comprising irregularly or regularly shaped ion-exchange resin particles with an ion-exchange capacity of less than about 6 meq/gram having particle sizes ranging from about 10 to about 500 microns, said particles having a pharmacologically active drug bound thereto wherein said drug comprises more than about 38% (for irregularly shaped particles) and 30% (for regularly shaped particles) by weight of the drug-resin complex and wherein said drug-resin complex particles have been subsequently coated with from about 1.5% to about 25% by weight of the drug-resin complex of a water-permeable diffusion barrier and wherein said composition provides controlled release of said active drug.

All percentages and ratios used herein are by weight unless otherwise indicated.

DESCRIPTION OF THE INVENTION

It has now been found that significant and controllable retardation of the release of pharmacologically active drugs into fluids similar to those found in the gastrointestinal tract can be achieved by the direct application of a water-permeable diffusion barrier to regularly or irregularly shaped particles of an ion-exchanger onto which a drug has been bound.

As used herein, the term water-permeable is used to indicate that the fluids of the alimentary canal will permeate or penetrate the coating film with or without dissolving the film or parts of the film. Depending on the permeability or solubility of the chosen coating (polymer or polymer mixture) a lighter or heavier application thereof is required so that the drug does not leach out from the complex to an extent of more than 4% in artificial saliva at 20°–40° C. in 2 minutes.

As used herein, the term regularly shaped particles refer to those particles which substantially conform to geometric shapes such as spherical, elliptical, cylindrical and the like. These shapes are ordered according to established geometric principles. For example, regularly shaped ion-exchange resins of this type are exemplified by Dow XYS-40010.00 and Dow XYS-40013.00 (both supplied by Dow Chemical Company), and to the drug-resin complexes formed by binding drugs to these resins.

As used herein, the term irregularly shaped particles refers to particles excluded from the above definition, such as those particles with amorphous shapes with increased surface areas due to surface area channels or distortions. For example, irregularly shaped ion-exchange resins of this type are exemplified by Amberlite IRP-69 supplied by Rohm and Haas), and to the drug-resin complexes formed by binding drugs to these resins.

The drugs that are suitable for use in these preparations are acidic, basic or amphoteric. Examples of acidic drugs useful in the present invention include, but are not limited to dehydrocholic acid, diflunisal, ethacrynic acid, fenoprofen, furosemide, gemfibrozil, ibuprofen, naproxen, phenytoin, probenecid, sulindac, theophylline, salicylic acid and acetylsalicylic acid. Examples of basic drugs useful in the present invention include, but are not limited to, acetophenazine, amitriptyline, amphetamine, benztropine, biperiden, bromodiphenhydramine, brompheniramine, carbinoxamine, chlorcyclizine, chlorpheniramine, chlorphenoxamine, chlorpromazine, clemastine, clomiphene, clonidine, codeine, cyclizine, cyclobenzaprine, cyproheptadine, desipramine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, maprotiline, meclizine, mepenzolate, meperidine, mephentermine, mesoridazine, methadone, methdilazine, methscopolamine, methysergide, metoprolol, nortriptylene, noscapine, nylindrin, orphenadrine, papaverine, pentazocine, phendimetrazine, phentermine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine and codeine. Examples of amphoteric drugs useful in the present invention include, but are not limited to, aminocaproic acid, aminosalicylic acid, hydromorphone, isoxsuprine, levorphanol, melphalan, morphine, nalidixic acid, and paraaminosalicylic acid.

The ion-exchange resins suitable for use in these preparations are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion-exchangers suitable for use in ion-exchange chromatography and for such applications as deionization of water are suitable for use in these controlled release drug preparations. Such ion-exchangers are described by H. F. Walton in "Principles of Ion Exchange" (pp. 312–343) and "Techniques and Applications of Ion-Exchange Chromatography" (pp. 344–361) in *Chromatoqraohy*. (E. Heftmann, editor), Van Nostrand Reinhold Company, New York (1975), incorporated by reference herein. The ion-exchange resins useful in the present invention have exchange capacities below about 6 meq./g. and preferably below about 5.5 meq./g.

The size of the ion-exchange particles should preferably fall within the range of about 40 μm to about 150 μm. Particle sizes substantially below the lower limit are difficult to handle in all steps of the processing. Particle sizes substantially above the upper limit, e.g., commercially-available ion-exchange resins having a spherical shape and diameters up to about 1000 μm, are gritty in liquid dosage forms and have a greater tendency to fracture when subjected to drying-hydrating cycles. Moreover, it is believed that the increased distance that a displacing ion must travel in its diffusion into these large particles, and the increased distance the displaced drug must travel in its diffusion out of these large particles, cause a measurable but not readily controlled prolongation of release even when the drug-resin complexes are uncoated. Release of drug from uncoated drug-resin complexes with particle sizes in the approximate range of 40 μm to 150 μm is relatively rapid. Satisfactory control of the release from such complexes is achieved almost exclusively by the applied diffusion barrier coating.

Representative resins useful in this invention include Amberlite IRP-69 (obtained from Rohm and Haas) and Dow XYS-40010.00 (obtained from The Dow Chemical Company). Both are sulfonated polymers composed of polystyrene cross-linked with 8% of divinylbenzene, with an ion-exchange capacity of about 4.5 to 5.5 milliequivalents per gram (meq./g) of dry resin ($H^+$-form). Their essential difference is in physical form. Amberlite IRP-69 consists of irregularly-shaped particles with a size range of 47 μm to 149 μm, produced by milling the parent large-sized spheres of Amberlite IRP-120. The Dow XYS-40010.00 product consists of spherical particles with a size range of 45 μm to 150 μm. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 milliequivalents per gram of dry resin.

Binding of drug to resin can be accomplished according to four general reactions. In the case of a basic drug, these are: (a) resin ($Na^{30}$-form) plus drug (salt form); (b) resin ($Na^{30}$-form) plus drug (as free base); (c) resin ($H^{30}$-form) plus drug (salt form); and (d) resin ($H^+$-form) plus drug (as free base). All of these reactions except (d) have cationic by-products and these by-products, by competing with the cationic drug for binding sites on the resin, reduce the amount of drug bound at equilibrium. For basic drugs, stoichiometric binding of drug to resin is accomplished only through reaction (d). Without being limited by theory, it is believed that the extent of drug binding is critical to the maintenance of the integrity of the diffusion barrier coating.

Four analogous binding reactions can be carried out for binding an acidic drug to an anion exchange resin. These are: (a) resin ($Cl^-$-form) plus drug (salt form); (b) resin ($Cl^-$-form) plus drug (as free acid); (c) resin ($OH^-$-form) plus drug (salt form); and (d) resin ($OH^-$-form) plus drug (as free acid). All of these reactions except (d) have ionic by-products and the anions generated when the reactions occur compete with the anionic drug for binding sites on the resin with the result that reduced levels of drug are bound at equilibrium. For acidic drugs, stoichiometric binding of drug to resin is accomplished only through reaction (d). The binding may be performed, for example, as a batch or column process, as is known in the art. In most of the illustrative examples described below, the drug-resin complexes are prepared by a batch process that is based on reaction (d). The drug-resin complex thus formed is collected by filtration and washed with ethanol to insure removal of any unbound drug. The complexes are usually air-dried in trays at room temperature.

Control of the release of drugs from drug-resin complexes has been achieved by the direct application of a diffusion barrier coating to particles of such complexes, provided that the drug content of the complexes was above a critical value. Any coating procedure which provides a contiguous coating on each particle of drug-resin complex without significant agglomeration of particles may be used. In all of the illustrative examples below, the coatings were applied with a fluid-bed coating apparatus having the Wurster configuration. Measurements of particle size distribution before and after coating showed that agglomeration of particles was insignificant.

The coating materials may be any of a large number of natural or synthetic film-formers used singly, in admixture with each other, and in admixture with plasticizers, pigments and other substances to alter the characteristics of the coating. In general, the major components of the coating should be insoluble in, and permeable to, water. However, it might be desirable to incorporate a water-soluble substance, such as methyl cellulose, to alter the permeability of the coating, or to incorporate an acid-insoluble, base-soluble substance to act as an enteric coating. The coating materials may be applied as a suspension in an aqueous fluid or as a solution in organic solvents. Suitable examples of such coating materials are described by R. C. Rowe in *Materials used in Pharmaceutical Formulation*. (A. T. Florence, editor), Blackwell Scientific Publications, Oxford, 1–36 (1984), incorporated by reference herein. Preferably the water-permeable diffusion barrier is selected from the group consisting of ethyl cellulose, methyl cellulose and mixtures thereof.

The coated drug-resin particles prepared according to the teachings of this invention are suitable for suspending in an essentially aqueous vehicle with the only restrictions on its composition being (i) an absence of, or very low levels of ionic ingredients, and (ii) a limitation on the concentrations of water-miscible organic solvents, such as alcohol, to those levels which do not cause dissolution of the diffusion barrier coating. These coated drug-resin particles are also suitable for placing into capsules as a solid dosage form.

Various oral dosage forms can be used, including such solid forms as tablets, capsules, granules, lozenges and bulk powders and liquid forms such as syrups and suspensions. These oral forms comprise a safe and effective amount, usually equivalent to at least about 0.1% of the coated drug-resin complex. Solid oral dosage forms preferably contain from about 5% to about 95%, more preferably from about 10% to about 95%, and most preferably from about 25% to about 95% of the drug-resin complex. Liquid oral dosage forms preferably contain from about 1% to about 50% and more preferably from about 1% to about 25% and most preferably from about 3% to about 10% of the drug-resin complex.

Tablets can be compressed, tablet triturates, enteric-coated, sugar-coated, film-coated or multiple compressed, containing suitable binders, lubricants, diluents, disintegrating agents, coloring agents, flavoring agents, preservatives and flow-inducing agents.

Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. Specific examples of pharmaceutically acceptable carriers and excipients that may be used to formulate oral dosage forms, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*. Vol. 7. (Banker and Rhodes, editors), 359–427 (1979), incorporated by reference herein. Techniques and compositions for making tablets (compressed and molded), capsules (hard and soft gelatin) and pills are described in *Remington's Pharmaceutical Sciences* (Arthur Osol, editor), 1553–1593 (1980), incorporated herein by reference.

In preparing the liquid oral dosage forms, the drug-resin complexes are incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. The most preferred carrier is a suspension of the pharmaceutical composition in an aqueous vehicle containing a suitable suspending agent. Suitable suspending agents include Avicel RC-591 (a microcrystalline cellulose/ sodium carboxymethyl cellulose mixture available from FMC), guar gum and the like. Such suspending agents are well known to those skilled in the art. While the amount of water in the compositions of this invention can vary over quite a wide range depending upon the total weight and volume of the drug-resin complex and other optional non-active ingredients, the total water content, based on the weight of the final composition, will generally range from about 20 to about 75%, and, preferably, from about 20 to about 40%, by weight/volume.

Although water itself may make up the entire carrier, typical liquid formulations preferably contain a co-solvent, for example, propylene glycol, glycerin, sorbitol solution and the like, to assist solubilization and incorporation of water-insoluble ingredients, such as flavoring oils and the like into the composition. In general, therefore, the compositions of this invention preferably contain from about 5 to about 25 volume/volume percent and, most preferably, from about 10 to about 20 volume/ volume percent, of the co-solvent.

The compositions of this invention may optionally contain one or more other known therapeutic agents, particularly those commonly utilized in cough/cold preparations, such as, for example, a decongestant such as pseudoephedrine hydrochloride, phenylpropanolamine HCl, phenylephrine hydrochloride and ephedrine hydrochloride; an analgesic such as acetaminophen and ibuprofen; an expectorant or mucolytic such as glyceryl guaiacolate, terpin hydrate, ammonium chloride, N-acetylcysteine and ambroxol; and an antihistamine such as chlorpheniramine maleate, doxylamine succinate, brompheniramine maleate and diphenhydramine hydrochloride: all of which are described in U.S. Pat. No. 4,619,934 to Sunshine et al., issued Oct. 28, 1986, which is incorporated by reference herein. Also useful are bronchodilators such as theophylline and albuterol.

Other optional ingredients well known to the pharmacist's art may also be included in amounts generally known for these ingredients, for example, natural or artificial sweeteners, flavoring agents, colorants and the like to provide a palatable and pleasant looking final product, antioxidants, for example, butylated hydroxy anisole or butylated hydroxy toluene, and preservatives, for example, methyl or propyl paraben or sodium benzoate, to prolong and enhance shelf life.

TEST METHOD

Moisture determinations were performed with a Mettler LP16 infrared heater on a PE160 balance. Because of the variation in moisture content over relatively short time periods, moisture determinations were always performed immediately prior to the use of any resin or drug-resin complex, and corrections were made in quantities taken so that all values are expressed on a dry weight basis.

Immediately after preparation, all drug-resin complexes were washed with an appropriate solvent to insure removal of unbound drug. When the salt forms of drugs were used in the binding mixture, water was used to wash the complex. When the free base or free acid forms of the drugs were used in the binding mixture, ethanol was used to wash the complex. Washing was continued in a batch or percolation mode until the washings were shown by spectrophotometric measurements to be essentially free of drug.

All complexes containing cationic drugs were analyzed for drug content by adding an accurately weighed sample (about 500 mg) to a 200 mL volumetric flack containing 100 mL of 0.5M sodium acetate in 90% ethanol and heating the mixture at reflux for one hour. For the complex containing the anionic drug, ibuprofen, the sample was added to a 200 mL volumetric flask containing 100 mL of 0.1N HCl in ethanol and similarly heated. The mixture was allowed to cool to room temperature and was diluted to 200 mL with ethanol. An aliquot was removed from the clear supernatant after settling or centrifugation. After appropriate dilution, the drug content of the supernatant was determined spectrophotometrically. Drug content of the complex was expressed as weight percentage based on the free base or the free acid form of the drug, unless otherwise indicated.

Determinations of release of drug from drug-resin complexes were performed with equipment that conforms to the USP Dissolution Apparatus 2. In all instances, a two-bladed paddle rotating at 50 rpm was used. Release media were used in a volume of 900 mL per dissolution vessel, maintained at 37° C., and were chosen to simulate gastric fluid (0.1N hydrochloric acid) or intestinal fluid (0.05M phosphate buffer, pH 7.2). In situ conversion of simulated gastric fluid to pH 7.2 buffer was accomplished by adding 24.8 g of trisodium phosphate dodecahydrate to 900 mL of 0.1N hydrochloric acid. Sufficient drug-resin complexes were added to provide the following doses (expressed as the commonly administered forms): dextromethorphan hydrobromide monohydrate, 60 mg; ibuprofen (free acid), 200 mg; phenylpropanolamine hydrochloride, 75 mg; and pseudoephedrine hydrochloride, 120 mg. The drug-resin complexes were added to the release media as dry powders or as previously prepared suspensions in 10 mL of distilled water to simulate an essentially ion-free liquid dosage form. At appropriate time intervals, samples of approximately 10 mL were removed from the dissolution beaker and immediately filtered through a syringe-mounted filter. Exactly 5.0 mL of the filtrate was reserved for analysis. The remainder of the resin complex adhering to the filter were rinsed into the dissolution beaker with exactly 5.0 mL of fresh release medium. The absorbances of the filtered samples were measured at the wavelength of the peak in the ultraviolet spectrum with a Perkin-Elmer model 552 or Lambda 3B uv/vis spectrophotometer. The absorbance values were converted to percentages of added drug that were released. Alternatively, the samples were analyzed by HPLC on a reverse phase phenyl column using methanol:water:acetic acid (50:50:3 by volume, with 5 mm sodium hexane sulfonate) with a Waters model 6000A pump and a model 450 variable wavelength detector set at the wavelength of peak absorption for the drug. Peak areas were converted to percentage of drug released.

Diffusion barrier coatings were applied with a Glatt CPCG-5 Wurster-type fluid-bed coater. The following were the conditions used in a typical coating procedure: inlet air temperature, 70° C.; atomization air pressure, 60 psi; spray rate, 20–25 g/min; outlet air temperature, 40°–50° C. Microscopic examination of the coated particles was performed with a light microscopic and with a scanning electron microscope. Particle size determinations of drug-resin complexes before and after coating were performed with a Malvern Series 2600C droplet and particle sizer.

The level of coating contained on the coated drug-resin complex was determined by stripping the coating with an appropriate solvent, evaporating the solvent, and weighing the dried residue. For the coatings that contained only ethylcellulose, an accurately weighed sample of coated drug-resin complex of about 2.0 g was placed in a 30-mL glass centrifuge tube. Twenty mL of ethanol was added and the mixture was stirred occasionally over a period of about 30 minutes. The mixture was centrifuged and the supernatant was decanted into a round bottom flask. The extraction, centrifugation and decanting were repeated three more times. The combined ethanolic extracts were concentrated to dryness in a rotary vacuum evaporator. The flask containing the dried residue was rinsed four times, each with several mL of methylene chloride/acetone (9:1 v/v). The rinsings were transferred to a tared aluminum pan and allowed to evaporate in a hood. The pan was heated at 55° C. for 30 minutes, allowed to cool, and weighed. For coatings that contained ethylcellulose and Myvacet 9-40 (an acetylated monoglyceride), the stripping solvent was methylene chloride/acetone (9:1 v/v). The increase over the tare weight was attributed to the ethylcellulose coating. The values obtained agreed very well with the amount of coating applied in the fluid-bed coater.

The following examples illustrate embodiments of the subject invention wherein both essential and optional ingredients are combined.

EXAMPLE I

A. Preparation of pseudoephedrine-Amberlite IRP-69 complex having a pseudoephedrine content of 38.2% by weight.

| | |
|---|---|
| Amberlite IRP-69 (H+-form) | 1400 g |
| Pseudoephedrine base | 857 g |

The resin was mixed with about 20 liters of distilled water. The pseudoephedrine base was added while the mixture was stirred. Stirring was continued for three hours. The mixture was filtered with a Buchner funnel and the drug-resin cake that was retained by the filter was washed with ethanol (approximately 8 liters) until the washings had a negligible absorbance at 257 nm. The drug-resin complex, washed free of unbound drug, was tray-dried at room temperature. Analysis showed that the complex contained 38.2% by weight of pseudoephedrine. The following release was shown by the drug-resin complex.

| Time (minutes) | % Pseudoephedrine released in 0.1 N HCl |
|---|---|
| 15 | 78 |
| 30 | 84 |
| 60 | 88 |
| 120 | 89 |
| 180 | 89 |

B. Coating of the drug-resin complex from (A) above:

| | |
|---|---|
| Pseudoephedrine-IRP-69 Complex from (A) | 2000 g |
| Ethylcellulose, N-10 | 170 g |
| Myvacet 9-40 | 30.0 g |
| Ethyl acetate | 3800.0 g |

The Myvacet 9-40, an acetylated monoglyceride, was dissolved in the ethyl acetate. The ethylcellulose was added to this solution and the mixture was stirred until the ethylcellulose was dissolved. The resin complex was placed in a pre-warmed fluid-bed coating apparatus and fluidized with 70° C. intake air. The coating solution was applied at a rate of 20–25 g/minute until 4000 g had been applied. Fluidization was continued with the heated air for an additional ten minutes after termination of the application of the coating solution. The release given by this coated complex was substantially less than that given by the uncoated complex from (A) above and by the coated complex from Example I at all sampling times. Moreover, its release closely paralleled that of the more highly loaded coated complex in Example II.

| Time (minutes) | % Pseudoephedrine released in 0.1 N HCl |
|---|---|
| 15 | 51 |
| 30 | 63 |
| 60 | 73 |
| 120 | 80 |
| 180 | 83 |

EXAMPLE II

A. Preparation of pseudoephedrine-Amberlite IRP-69 complex having a pseudoephedrine content of 48.0% by weight:

| | |
|---|---|
| Amberlite IRP-69 (H+-form) | 6827 g |
| Pseudoephedrine base | 5869 g |

The resin was mixed with about 20 liters of distilled water. The pseudoephedrine base was added while the mixture was stirred. Stirring was continued for three hours. The mixture was filtered with a Buchner funnel and the drug-resin cake that was retained by the filter was washed with ethanol (approximately 8 liters) until the washings had a negligible absorbance at 257 nm. The drug-resin complex, washed free of unbound drug, was tray-dried at room temperature. Analysis showed that the complex contained 48.0% by weight of pseudoephedrine. The following release was shown by the uncoated drug-resin complex.

| Time (minutes) | % Pseudoephedrine released in 0.1 N HCl |
|---|---|
| 15 | 83 |
| 30 | 86 |
| 60 | 89 |
| 120 | 94 |
| 180 | 93 |

B. Coating of the drug-resin complex from (A) above:

| | |
|---|---|
| Pseudoephedrine-IRP-69 Complex from (A) | 2000 g |
| Ethylcellulose, N-10 | 170 g |
| Myvacet 9-40 | 30.0 g |
| Ethyl acetate | 3800 g |

The Myvacet 9-40, an acetylated monoglyceride, was dissolved in the ethyl acetate. The ethylcellulose was added to this solution and the mixture was stirred until the ethylcellulose was dissolved. The resin complex was placed in a pre-warmed fluid-bed coating apparatus and fluidized with 70° C. intake air. The coating solution was applied at a rate of 20–25 g/minute until 4000 g had been applied. Fluidization was continued with the heated air for an additional ten minutes after termination of the application of the coating solution. Release of drug from this coated complex is shown below.

| Time (minutes) | % Pseudoephedrine released in 0.1 N HCl |
|---|---|
| 15 | 36 |
| 30 | 54 |
| 60 | 69 |
| 120 | 79 |
| 180 | 75 |

EXAMPLE III

A. Preparation of pseudoephedrine-Amberlite IRP-69 complex having a pseudoephedrine content of 40.7% by weight.

| | |
|---|---|
| Amberlite IRP-69 (H+-form) | 1400 g |

| | |
|---|---|
| -continued | |
| Pseudoephedrine base | 865 g |

The resin was mixed with about 20 liters of distilled water. The pseudoephedrine base was added while the mixture was stirred. Stirring was continued for three hours. The mixture was filtered with a Buchner funnel and the drug-resin cake that was retained by the filter was washed with ethanol (approximately 8 liters) until the washings had a negligible absorbance at 257 nm. The drug-resin complex, washed free of unbound drug, was tray-dried at room temperature. Analysis showed that the complex contained 40.7% by weight of pseudoephedrine. The following release was shown by the drug-resin complex.

| Time (minutes) | % Pseudoephedrine released in 0.1 N HCl |
|---|---|
| 15 | 78 |
| 30 | 82 |
| 60 | 83 |
| 120 | 83 |
| 180 | 84 |

B. Coating of the drug-resin complex from (A) above:

| | |
|---|---|
| Pseudoephedrine-IRP-69 Complex from (A) | 2000 g |
| Ethylcellulose, N-10 | 300 g |
| Ethyl acetate | 5700 g |

The ethylcellulose was dissolved in the ethyl acetate. The resin was placed in a pre-warmed fluid-bed coating apparatus and fluidized with 70° C. intake air. The coating solution was applied at a rate of 20-25 g/minute until 6000 g had been applied. Fluidization was continued with the heated air for an additional ten minutes after termination of the application of the coating solution. The following release was obtained for this coated complex.

| Time (minutes) | % Pseudoephedrine released in 0.1 N HCl |
|---|---|
| 15 | 12 |
| 30 | 18 |
| 60 | 25 |
| 120 | 34 |
| 180 | 39 |

These results show that there is a substantial retardation of release with this coated complex.

EXAMPLE IV

This example illustrates the effect of three levels of coating on the release of drug. The core complex used for coating was the same as that whose preparation was described in Example II.

A. Application of various levels of coating to the complex from Example II.

| | |
|---|---|
| Pseudoephedrine-IRP-69 Complex from Example II | 2000 g |
| Ethylcellulose, N-10 | 400 g |
| Ethyl acetate | 7600 g |

The ethylcellulose was dissolved in the ethyl acetate with stirring. The complex was placed in a pre-warmed fluid-bed coating apparatus and fluidized with 70° C. intake air. The coating solution was applied at a rate of 20-25 g/minute until 4000 g had been applied. A sample of approximately 10 g of the resin complex having an applied coating of 10% by weight was removed through a sampling port. Application of the coating solution was resumed with brief cessations and sampling of the coated complex after 6 6000 g and 8000 g had been applied as a percentage of the weight of the complex, were 15.0 and 20.0% respectively. The releases given by these variously coated complexes were as follows.

| Time (minutes) | % Pseudoephedrine released in 0.1 N HCl | | |
|---|---|---|---|
| | 10.0% Coating | 15.0% Coating | 20.0% Coating |
| 15 | 33 | 23 | 10 |
| 30 | 39 | 31 | 13 |
| 60 | 49 | 41 | 18 |
| 120 | 62 | 50 | 24 |
| 180 | 69 | 56 | 28 |
| 240 | 73 | 66 | 36 |

These release profiles clearly demonstrate that an increase in the amount of coating applied to the resin complex causes an increase in the retardation of drug release. Comparison of the release profile given by a 10% applied coating of ethylcellulose with that given by the same level of ethylcellulose plus plasticizer as in Example II indicates that omission of the plasticizer results in a greater retardation of drug release.

EXAMPLE V

A. Preparation of phenylpropanolamine-Amberlite IRP-69 complex having a phenylpropanolamine content of 44.7% by weight.

| | |
|---|---|
| Amberlite IRP-69 (H⁺-form) | 1286 g |
| Phenylpropanolamine base | 1019 g |

The resin was mixed with about 20 liters of distilled water. The phenylpropanolamine base was added while the mixture was stirred. Stirring was continued for three hours. The mixture was filtered with a Buchner funnel and the drug-resin cake that was retained by the filter was washed with ethanol (approximately 8 liters) until the washings had a negligible absorbance at 257 nm. The drug-resin complex, washed free of unbound drug, was tray-dried at room temperature. Analysis showed that the complex contained 44.7% by weight of phenylpropanolamine. The following release was shown by the uncoated complex.

| Time (minutes) | % Phenylpropanolamine released in 0.1 N HCl |
|---|---|
| 15 | 91 |
| 30 | 94 |
| 60 | 99 |
| 120 | 104 |
| 180 | 103 |

B. Coating of the drug-resin complex from (A) above:

| | |
|---|---|
| Phenylpropanolamine-IRP-69 Complex from (A) | 2000 g |
| Ethylcellulose, N-10 | 300 g |

-continued

| | |
|---|---|
| Ethyl acetate | 5700 g |

The ethylcellulose was dissolved in the ethyl acetate with stirring. The resin complex was placed in a pre-warmed fluid-bed coating apparatus and fluidized with 70° C. intake air. The coating solution was applied at a rate of 20–25 g/minute until 6000 g had been applied. Fluidization was continued with the heated air for an additional 10 minutes after termination of the application of the coating solution. The release given by the coated complex is shown below.

| Time (minutes) | % Phenylpropanolamine released in 0.1 N HCl |
|---|---|
| 15 | 24 |
| 30 | 27 |
| 60 | 42 |
| 120 | 46 |
| 180 | 53 |
| 240 | 65 |

The release of phenylpropanolamine is substantially retarded compared to that of the uncoated complex and is very similar to that given by the pseudoephedrine-IRP-69 complex coated at the same level (15%) in the previous example.

EXAMPLE VI

A. Preparation of pseudoephedrine-Dow resin complex having a pseudoephedrine content of 47.2% by weight:

| | |
|---|---|
| Dow XYS-40010.00 Resin (H+-form) | 4312 g |
| Pseudoephedrine base | 3814 g |

The resin was mixed with about 20 liters of distilled water. The pseudoephedrine base was added while the mixture was stirred. Stirring was continued for three hours. The mixture was filtered with a Buchner funnel and the drug-resin cake that was retained by the filter was washed with ethanol (approximately 8 liters) until the washings had a negligible absorbance at 257 nm. The drug-resin complex, washed free of unbound drug, was tray-dried at room temperature. Analysis showed that the complex contained 47.2% by weight of pseudoephedrine. The following release was given by this uncoated complex.

| Time (minutes) | % Pseudoephedrine released in 0.1 N HCl |
|---|---|
| 15 | 84 |
| 30 | 88 |
| 60 | 90 |
| 120 | 90 |
| 180 | 91 |

Coating of the drug-resin complex from (A) above:

| | |
|---|---|
| Pseudoephedrine-resin complex from (A) | 2000 g |
| Ethylcellulose, N-10 | 100 g |
| Ethyl acetate | 1900 g |

The ethylcellulose was dissolved in the ethyl acetate with stirring. The complex was placed in a pre-warmed fluid-bed coating apparatus and fluidized with 70° C. intake air. The coating solution was applied at a rate of 20–25 g/minute until 1000 g had been applied. A sample of approximately 10 g of the resin complex having an applied coating of 2.5% by weight was removed through a sampling port. Application of the coating solution was resumed until 2000 g had been applied. The releases shown by these coated complexes are presented below.

| Time (minutes) | % Pseudoephedrine released in 0.1 N HCl | |
|---|---|---|
| | 2.5% Coating | 5.0% Coating |
| 15 | 22 | 5 |
| 30 | 24 | 7 |
| 60 | 34 | 12 |
| 120 | 44 | 19 |
| 180 | 53 | 23 |
| 240 | — | 25 |

This example illustrates the successful application of a diffusion barrier coating to a drug-resin complex in which the resin is chemically the same as the Amberlite IRP-69 resin, but is different in its physical form. The Dow XYS-40010.00 resin used in this example is supplied as spherical particles with a size range of 45 μm to 150 μm. Application of a 5% coating of ethylcellulose resulted in a strong retardation of drug release.

The following example illustrates the effect on coating integrity when the drug content of complexes made with the spherical resin is decreased.

EXAMPLE VII

A. Preparation of pseudoephedrine-Dow resin complex having a pseudoephedrine content of 33.0% by weight.

| | |
|---|---|
| Dow XYS-40010.00 resin (H+-form) | 1500 g |
| Pseudoephedrine-Dow resin complex (46.4% pseudoephedrine by weight) | 3000 g |

The resin and drug-resin complex were combined with 7.5 liters of 0.1 Normal hydrochloric acid. The mixture was allowed to stand 6 days with occasional stirring. The supernatant liquid was decanted and the drug-resin cake was washed free of unbound drug with water and then with ethanol The complex was then spread on trays and air-dried at room temperature. Analysis showed that the complex contained 33.0% by weight of pseudoephedrine.

The following release was shown by the uncoated complex.

| Time (minutes) | % Pseudoephedrine released in 0.1 N HCl |
|---|---|
| 15 | 57 |
| 30 | 61 |
| 60 | 71 |
| 120 | 80 |
| 180 | 83 |
| 240 | 87 |

B. Coating of the drug-resin complex from (A) above.

| | |
|---|---|
| Pseudoephedrine-Dow resin complex from (A) | 1000 g |
| Ethylcellulose, N-10 | 50 g |

-continued

| | |
|---|---|
| Ethyl acetate | 950 g |

The ethylcellulose was dissolved in the ethyl acetate with stirring. The complex was placed in a pre-warmed fluid-bed coating apparatus and fluidized with 70° C. intake air. The coating solution was applied at a rate of 20-25 g/minute until 500 g had been applied. A sample of approximately 10 g of the resin complex having an applied coating of 2.5% by weight was removed through a sampling port. Application of the coating solution was resumed until 1000 g had been applied. The releases shown by these coated complexes are presented below.

| Time (minutes) | % Pseudoephedrine released in 0.1N HCl | |
|---|---|---|
| | 2.5% Coating | 5.0% Coating |
| 15 | 35 | 20 |
| 30 | 48 | 28 |
| 60 | 60 | 37 |
| 120 | 68 | 46 |
| 180 | 71 | 50 |
| 240 | 74 | 54 |

Despite the low drug content of this complex, the coating was effective in causing a substantial reduction in the release of drug.

EXAMPLE VIII

A. Preparation of a dextromethorphan-Dow resin complex having a dextromethorphan content of 56.2% by weight.

| | |
|---|---|
| Dow-XYS-40010.00 resin (H+-form) | 2000 g |
| Dextromethorphan base | 2478 g |

The resin was added to about 20 liters of distilled water that had previously been heated to 90°-100° C. in a 70-liter glass reaction vessel equipped with a heating mantle, a stirrer and a condenser. The dextromethorphan base was added and the mixture was stirred for about one hour while maintaining the elevated temperature. Heating was discontinued and stirring was continued until the mixture cooled to 40°-50° C. The contents of the vessel were pumped into a suitable non-reactive plastic container and then filtered with a Buchner funnel. The drug-resin cake that was retained by the filter was washed with ethanol (approximately 10 liters) until the washings had a negligible absorbance at 278 nm. The drug-resin complex, washed free of unbound drug, was tray-dried at room temperature. Analysis showed that the complex contained 56.2% by weight of dextromethorphan. The uncoated drug-resin complex gave the following release of drug.

| Time (minutes) | % Dextromethorphan released in 0.1N HCl |
|---|---|
| 15 | 24 |
| 30 | 33 |
| 60 | 44 |
| 120 | 56 |
| 180 | 63 |

B. Coating of the drug resin complex from (A) above:

| | |
|---|---|
| Dextromethorphan-Dow resin complex from (A) | 2000 g |
| Ethylcellulose, N-50 | 119 g |
| Myvacet 9-40 | 11 g |
| Ethanol | 2470 g |

The Myvacet was dissolved in the ethanol. The ethylcellulose was added to this solution and the mixture was stirred until the ethylcellulose was dissolved. The resin complex was placed in a pre-warmed fluid-bed coating apparatus and fluidized with 70° C. intake air. The coating solution was applied at a rate of 20-25 g/minute until 700 g had been applied. A sample of approximately 10 g of the resin complex having an applied coating of 1.75% by weight was removed through a sampling port. Application of the coating solution was resumed with a brief cessation and sampling after 1760 g had been applied. Coating was then continued until 2600 g of coating solution had been applied. The releases given by these variously coated complexes are shown below.

| Time (minutes) | % Dextromethorphan released in 0.1N HCl | | |
|---|---|---|---|
| | 1.75% Coating | 4.4% Coating | 6.5% Coating |
| 15 | 8 | 7 | 4 |
| 30 | 11 | 9 | 6 |
| 60 | 19 | 15 | 11 |
| 120 | 33 | 28 | 19 |
| 180 | 41 | 35 | 25 |

These results show that all levels of coating were effective in retarding the release of dextromethorphan and that increasing the level of coating caused greater retardation of release.

EXAMPLE IX

This example illustrates the application of this invention to a coated complex consisting of an anionic drug bound to an anion exchange resin. The drug used is ibuprofen, bound as its carboxylate anion. The resin is Dow XYS-40013.00, an anion exchange resin possessing a quaternary ammonium functional group and supplied in the form of spheres with a particle size range of approximately 50 μm to 150 μm.

A. Preparation of ibuprofen-Dow resin complex having an ibuprofen content of 29.6% by weight:

| | |
|---|---|
| Dow XYS-40013.00 resin (OH−-form) | 1240 g |
| Ibuprofen | 766 g |

The resin was mixed with about three liters of ethanol. The ibuprofen was added while the mixture was stirred. The mixture was allowed to stand for four days at room temperature. The ethanolic supernatant was decanted. The residue was stirred with 3 liters of fresh ethanol and allowed to settle. The ethanolic supernatant was decanted. The residue was mixed with 3 liters of ethanol and the slurry was filtered with a Buchner funnel. The drug-resin cake that was retained by the filter was washed with ethanol until the washings had a negligible absorbance at 264 nm. The drug-resin complex, washed free of unbound drug, was tray-dried at room temperature. Analysis showed that the complex contained 29.6% by weight of ibuprofen. The release given by the uncoated drug-resin complex is shown below.

| Time (minutes) | % Ibuprofen released in 0.05M phosphate buffer, pH 7.2 |
|---|---|
| 15 | 32 |
| 30 | 38 |
| 60 | 45 |
| 120 | 48 |
| 180 | 49 |
| 300 | 50 |

B. Coating of the drug-resin complex from (A) above:

| Ibuprofen-Dow resin complex from (A) | 1000 g |
|---|---|
| Ethylcellulose, N-10 | 25 g |
| Ethyl acetate | 475 g |

The ethylcellulose was dissolved in the ethyl acetate with stirring. The drug-resin complex was placed in a pre-warmed fluid-bed coating apparatus and fluidized with 70° C. intake air. The coating solution was applied at a rate of 20–25 g/minute until 500 g had been applied. The coated complex showed the following release.

| Time (minutes) | % Ibuprofen released in 0.05M phosphate buffer, pH 7.2 |
|---|---|
| 15 | 4 |
| 30 | 6 |
| 60 | 10 |
| 120 | 14 |
| 180 | 18 |
| 300 | 24 |

EXAMPLE X

A. Preparation of a pseudoephedrine-Dow resin complex having a pseudoephedrine content of 47.25% by weight.

| Dow XYS-40010.00 resin (H+-form) | 6000 g |
|---|---|
| Pseudoephedrine base | 5550 g |

The resin was mixed with about 60 liters of distilled water. The pseudoephedrine base was added while the mixture was stirred. Stirring was continued for three hours. The mixture was filtered in three portions with Buchner funnels and the drug-resin cakes that were retained by the filters were each washed with ethanol (approximately 8 liters) until the washings had a negligible absorbance at 257 nm. The drug-resin complex, washed free of unbound drug, was tray-dried at room temperature. Analysis showed that the complex contained 47.25% by weight of pseudoephedrine. The release given by this complex is shown below.

| Time (minutes) | % Pseudoephedrine released in 0.1N HCl |
|---|---|
| 15 | 84 |
| 30 | 88 |
| 60 | 88 |
| 120 | 90 |
| 180 | 90 |
| 240 | 91 |

B. Coating of the drug-resin complex from (A) above:

| Pseudoephedrine-Dow resin complex from (A) | 2000 g |
|---|---|
| Ethylcellulose, N-10 | 50 g |
| Ethyl acetate | 950 g |

The ethylcellulose was dissolved in the ethyl acetate with stirring. The complex was placed in a pre-warmed fluid-bed coating apparatus and fluidized with 70° C. intake air. The coating solution was applied at a rate of 20–25 g/minute until 1000 g had been applied. A second coating run was made with another 2000 g portion of the complex from (A) as described above. A third coating run was made as described above, but with the following quantities of complex from (A) and coating solution.

| Pseudoephedrine-Dow resin complex from (A) | 3000 g |
|---|---|
| Ethylcellulose, N-10 | 75 g |
| Ethyl acetate | 1425 g |

The releases obtained with each of these coated complexes are shown below.

| Time (minutes) | % Pseudoephedrine released in 0.1N HCl | | |
|---|---|---|---|
| | Coating Run 1 | Coating Run 2 | Coating Run 3 |
| 30 | 31 | 31 | 35 |
| 60 | 40 | 41 | 44 |
| 180 | 60 | 59 | 65 |
| 360 | 72 | 74 | 79 |

The release given by the coated complex from coating run 3 in 0.05M phosphate buffer, pH 7.2 is shown below together with the releases given by two blends of this coated complex with uncoated complex from (A).

| % in blend | | % Pseudoephedrine released in phosphate buffer | | | | | |
|---|---|---|---|---|---|---|---|
| Coated | Uncoated | 15 min | 30 min | 60 min | 120 min | 180 min | 240 min |
| 100 | 0 | 22 | 33 | 47 | 62 | 64 | 66 |
| 80 | 20 | 36 | 45 | 55 | 66 | 70 | 75 |
| 60 | 40 | 46 | 52 | 62 | 69 | 75 | 78 |

These results demonstrate that the coating process is capable of providing coatings that perform consistently in controlling the release of drug. For the coated complex from coating run 3, good agreement was found between the release in 0.1N HCl and in pH 7.2 phosphate buffer. The ability to alter the release profile so as to provide a loading dose of drug is demonstrated by the results obtained with the blends of coated and uncoated complexes.

EXAMPLE XI

A hardshell gelatin capsule for oral administration of the present invention is made as follows:

| INGREDIENTS | AMOUNT |
|---|---|
| Coated drug-resin complex of Example III | 276.9 mg |
| Lactose | 280.3 mg |
| Magnesium stearate | 2.8 mg |

The ingredients are dry blended and encapsulated in a #1 hardshell gelatin capsule using techniques as are known in the art.

EXAMPLE XII

A tablet for oral administration is made as follows:

| INGREDIENTS | AMOUNT |
|---|---|
| Coated drug-resin complex of Example III | 276.9 mg |

| INGREDIENTS | AMOUNT |
| --- | --- |
| Lactose | 238.1 mg |
| Maltodextrin | 50.0 mg |
| Croscarmelose | 25.0 mg |
| Magnesium Stearate | 5.0 mg |

The drug-resin complex and lactose are dry-blended and then granulated with a 10% aqueous solution of the maltodextrin. The resulting granulation is dried at 45° C. overnight. The dry granulation is milled and blended with the croscarmelose and the magnesium stearate. The resulting powder blend is compressed into 595 mg tablets.

EXAMPLE XIII

A chewable tablet for oral administration is made as follows:

| INGREDIENTS | AMOUNT |
| --- | --- |
| Coated drug-resin complex of Example III | 276.9 mg |
| Crystalline Sorbitol | 276.9 mg |
| Maltodextrin | 55.5 mg |
| Magnesium Stearate | 6.2 mg |
| Color and Flavor | qs |

The drug-resin complex and the sorbitol are dry-blended and then granulated with a 10% aqueous solution of the maltrodextrin. The resulting granule is dried at a temperature of about 45° C. overnight. The dry granule is milled and blended with remaining components. The resulting powder blend is compressed into 615.5 mg tablets secundum artem.

EXAMPLE XIV

A suspension fororal administration is made as follows:

| INGREDIENTS | AMOUNT |
| --- | --- |
| Sucrose | 6000.0 mg |
| Xanthan gum | 50.0 mg |
| Coated drug-resin complex of Example III | 276.9 mg |
| Methyl Paraben | 15.0 mg |
| Glycerin | 500.0 mg |
| Polysorbate 80 | 0.2 mg |
| Flavorant | 12.0 mg |
| Colorant | 0.2 mg |
| Water, purified qs ad | 10.0 ml |

The above ingredients are combined to produce a suspension, such that 10.0 mL will provide an adult human in need of such treatment with pseudoephedrine equivalent to 120 mg of pseudoephedrine hydrochloride, thereby providing decongestion for 12 hours.

What is claimed is:

1. An oral pharmaceutical composition in unit dosage form consisting essentially of irregularly shaped ion-exchange resin particles with an ion-exchange capacity of less than about 6 meq/gram having particle sizes ranging from about 10 to about 500 microns, said particles having a pharmacologically active drug bound thereto wherein said rug comprises more than about 38% by weight of the drug-resin complex, the ratio of pharmacologically-active drug to resin ranging from about 0.5:1 to about 1.5:1 and wherein said drug-resin complex particles have been subsequently coated with from about 1.5% to about 25% by weight of the drug-resin complex of a water-permeable diffusion barrier and wherein said composition provides controlled release of said active drug.

2. A pharmaceutical composition according to claim 1 wherein said irregularly shaped particles range from about 35 microns to about 150 microns.

3. A pharmaceutical composition according to claim 2 wherein said irregularly shaped particles range from about 40 microns to about 80 microns.

4. A pharmaceutical composition according to claim 3 wherein the ratio of pharmacologically-active drug ranges from about 0.8:1 to about 1.5:1.

5. A pharmaceutical composition according to claim 4 wherein said pharmacologically-active drug is selected from the group consisting of dehydrocholic acid, diflunisal, ethacrynic acid, fenoprofen, furosemide, gemfibrozil, ibuprofen, naproxen, phenytoin, probenecid, sulindac, theophylline, salicylic acid, acetylsalicylic acid, acetophenazine, amitriptyline, amphetamine, benztropine, biperiden, bromodiphenhydramine, brompheniramine, carbinoxamine, chlorcyclizine, chlorpheniramine, chlorphenoxamine, chlorpromazine, clemastine, clomiphene, clonidine, codeine, cyclizine, cyclobenzaprine, cyproheptadine, desipramine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, maprotiline, meclizine, mepenzolate, meperidine, mephentermine, mesoridazine, methadone, methdilazine, methscopolamine, methysergide, metoprolol, nortriptylene, noscapine, nylindrin, orphenadrine, papaverine, pentazocine, phendimetrazine, phentermine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine, codeine, aminocaproic acid, aminosalicylic acid, hydromorphone, isoxsuprine, levorphanol, melphalan, morphine, nalidixic acid, and paraaminosalicylic acid and mixtures thereof.

6. A pharmaceutical composition according to claim 5 wherein said resin particles have an ion-exchange capacity of less than about 5.5 meq./g.

7. A pharmaceutical composition according to claim 6 wherein the ratio of pharmacologically-active drug to resin ranges from about 1:1 to about 1.5:1.

8. A pharmaceutical composition according to claim 7 wherein said water-permeable diffusion barrier is selected from the group consisting of ethyl cellulose, methyl cellulose and mixtures thereof.

9. An oral pharmaceutical composition of unit dosage form consisting essentially of regularly shaped ion-exchange resin particles with an ion-exchange capacity of less than about 6 meq/gram having particle sizes ranging from about 10 to about 500 microns, said particles having a pharmacologically active drug bound thereto wherein said drug comprises more than about 30% by weight of the drug-resin complex, the ratio of pharmacologically-active drug to resin ranging from about 0.4:1 to about 1.5:1 and wherein said drug-resin complex particles have been subsequently coated with from about 1.5% to about 25% by weight of the drug-resin complex of a water-permeable diffusion barrier and wherein said composition provided controlled release of said active drug.

10. A pharmaceutical composition according to claim 9 wherein said regularly shaped particles range from about 35 microns to about 150 microns.

11. A pharmaceutical composition according to claim 10 wherein said regularly shaped particles range from about 40 microns to about 80 microns.

12. A pharmaceutical composition according to claim 11 wherein the ratio of pharmacologically-active drug ranges from about 0.8:1 to about 1:51.

13. A pharmaceutical composition according to claim 12 wherein said pharmacologically-active drug is selected from the group consisting of dehydrocholic acid, diflunisal, ethacrynic acid, fenoprofen, furosemide, gemfibrozil, ibuprofen, naproxen, phenytoin, probenecid, sulindac, theophylline, salicylic acid, acetylsalicylic acid, acetophenazine, amitriptyline, amphetamine, benztropine, biperiden, bromodiphenhydramine, brompheniramine, carbinoxamine, chlorcyclizine, chlorpheniramine, chlorphenoxamine, chlorpromazine, clemastine, clomiphene, clonidine, codeine, cyclizine, cyclobenzaprine, cyproheptadine, desipramine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, maprotiline, meclizine, mepenzolate, meperidine, mephentermine, mesoridazine, methadone, methdilazine, methscopolamine, methysergide, metoprolol, nortriptylene, noscapine, nylindrin, orphenadrine, papaverine, pentazocine, phendimetrazine, phentermine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine, codeine, aminocaproic acid, aminosalicylic acid, hydromorphone, isoxsuprine, levorphanol, melphalan, morphine, nalidixic acid, and paraaminosalicylic acid and mixtures thereof.

14. A pharmaceutical composition according to claim 13 wherein said resin particles have an ion-exchange capacity of less than about 5.5 meq./g.

15. A pharmaceutical composition according to claim 14 wherein the ratio of pharmacologically-active drug resin ranges from about 1:1 to about 1.5:1.

16. A pharmaceutical composition according to claim 15 wherein said water-permeable diffusion barrier is selected from the group consisting of ethyl cellulose, methyl cellulose and mixtures thereof.

* * * * *